Figure 1:
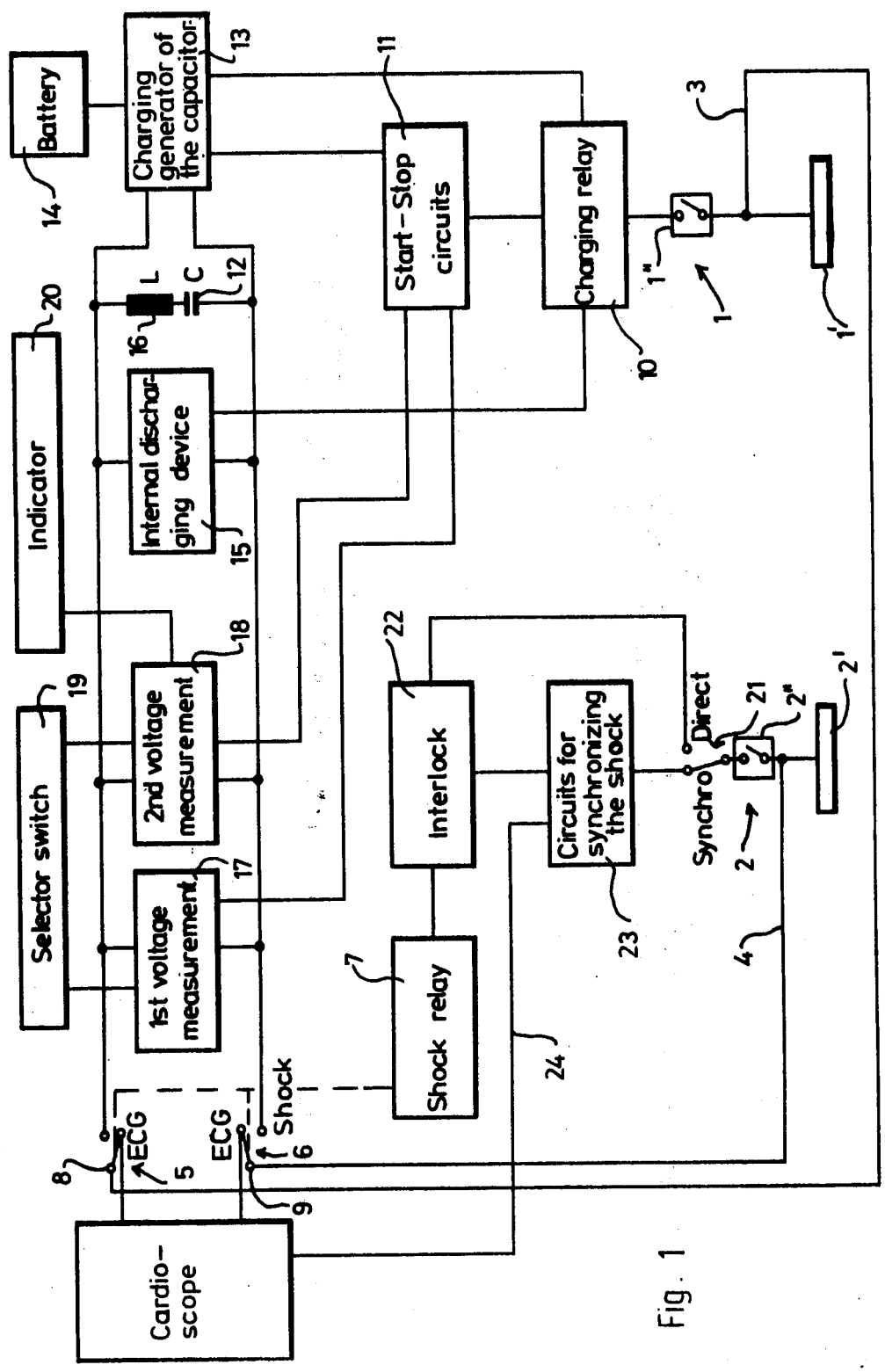

United States Patent [19]

Cansell

[11] 4,165,749

[45] Aug. 28, 1979

[54] MEDICAL DEVICE FOR ELECTROSHOCK THERAPY

[75] Inventor: Albert Cansell, Altenstadt, France

[73] Assignee: Bruker-Medizintechnik GmbH, Rheinstetten-Forchheim, Fed. Rep. of Germany

[21] Appl. No.: 844,619

[22] Filed: Oct. 25, 1977

[30] Foreign Application Priority Data

Nov. 9, 1976 [DE] Fed. Rep. of Germany ....... 2651031

[51] Int. Cl.² ............................................. A61N 1/36
[52] U.S. Cl. ............................................... 128/419 D
[58] Field of Search ...................... 128/419 D, 419 PG

[56] References Cited

U.S. PATENT DOCUMENTS

| | | | |
|---|---|---|---|
| 3,513,850 | 5/1970 | Weber | 128/419 D |
| 3,547,108 | 12/1970 | Seiffert | 128/419 D |
| 3,775,658 | 11/1973 | Miles | 128/419 D |

*Primary Examiner*—William E. Kamm

[57] ABSTRACT

A medical device for electroshock therapy, and more particularly a defibrillator for the treatment of ventricular and auricular fibrillation. Devices of this kind contain a high-voltage generator comprising a transformer with a rectifier connected to its output for charging a shunt capacitor which can be discharged through the patient by means of electrodes connected to it. In order to avoid by simple means the occurrence of dangerous leakage currents and in order to simplify the solving of the problem of high-voltage insulation, the rectifier comprises two branch circuits which are connected to a common transformer winding and which feed the shunt capacitor; furthermore, a high-impedance voltage divider is connected in parallel to the shunt capacitor with its center connected to chassis.

5 Claims, 3 Drawing Figures

MEDICAL DEVICE FOR ELECTROSHOCK THERAPY

The present invention relates to a medical device for electroshock therapy, and more particularly to a defibrillator for the treatment of ventricular and auricular fibrillation, with a high-voltage generator comprising a transformer with a rectifier connected to its output for charging a shunt capacitor which can be discharged through the patient by means of electrodes connected to its terminals.

Devices of this kind are used to administer electric shocks to a patient if, after a cardiac infarction for example, ventricular fibrillation occurs which unless treated immediately can result in the patient's death. Devices of this kind can also be used to therapeutically treat patients suffering from auricular fibrillation or supraventricular tachycardia. For this purpose, the shunt capacitor or defibrillation capacitor is charged to a voltage level of several kV. In general, the maximum energy is about 400 joule and can be reduced in steps by decreasing the maximum charging voltage. Electrodes with high-tension insulated handles and similarly insulated feeder cables are used to transfer the electrical energy to the patient. When the shock is effected, both terminals of the capacitor are connected to the feeder cables and thus to the electrodes. During charging, its two terminals are connected to the high-voltage generator.

A single shock or shunt capacitor is used for grading the various shock energies and the different quantities of energy are set by controlling the charging voltage. Accurate measurement of the voltage on the capacitor is necessary for this, and it also indicates that capacitor discharge has taken place during shock therapy. Problems arise here from the high voltage on the capacitor and from the requirement for dependably avoiding leakage currents from the patient or doctor to the device. If one terminal of the capacitor is connected to chassis or if one terminal of the voltmeter or the voltage measuring circuit is connected to chassis, then all parts connected to the other terminal must be dependably insulated to chassis against the full charging voltage. Although it is technically an easy matter to provide such an insulation, the space available is so limited in medical devices of the portable rather than the stationary type that it is extremely difficult to insulate against high voltages. The permissible currents which are drawn from the capacitor when making voltage measurements and when driving auxiliary circuits are very low. This means that all circuits must be of very high impedance. Equally, high-class insulation is necessary in order to keep the leakage currents sufficiently small. One possibility is to use a floating measuring arrangement, such as an ungrounded measuring instrument for example. Indicating instruments of this kind are expensive however, and they necessitate considerable extra expense if switching and control commands, for instance for voltage limitation, are to be taken from the meter. Another possibility is to establish a measurement reference point only while making measurements, but which is opened while the shock is being applied. A disadvantage of this, however, is that no voltage measurement is performed during the shock and thus the discharge process of the capacitor cannot be monitored. Furthermore, high voltage peaks can arise in the circuit. Finally, in all those cases where a signal is also taken simultaneously from the electrodes for an electrocardioscope, it is a disadvantage that four-terminal switchover is required, namely two terminals for two-terminal disconnection of the lead to the electrocardioscope and two terminals for connecting the two capacitor terminals at the electrodes. Since this switchover is effected by a relay which must be designed for the high voltage of several kV, the relay is large and expensive. For the present application, however, suitable vacuum relays are available commercially only in the form of two-terminal change-over switches.

The object of the present invention is to specify a circuit in which the disadvantages described above are overcome and in which in particular the problem of high-voltage insulation and the occurrence of dangerous leakage currents is simplified or solved.

According to the present invention, this object is solved with a device of the type mentioned at the outset in that the rectifier comprises two branch circuits which are connected to a common winding of the transformer and supply the shunt capacitor, in that a high impedance voltage divider is provided in parallel to the shunt capacitor, and in that the center of the voltage divider is connected to chassis. As a result of using two rectifier branches connected to a winding in conjunction with the voltage divider connected to chassis in its center region, the maximum voltage to be insulated against chassis or parts which can be contacted is halved. Consequently, the space problems due to the insulation requirements in a small portable device can be solved much more easily. Owing to the high impedance value of the connection between chassis and each of the two capacitor terminals, dangerous leakage currents cannot occur. The doctor need not fear that he himself will receive an electric shock when the shock treatment is applied; for if a not very high impedance connection exists from one terminal of the capacitor to chassis while the shock treatment is applied, then it is possible for a leakage current to flow to the other terminal of the capacitor, through the doctor for example, if he touches the patient in the vicinity of an electrode plate, as a result of which the circuit can close through ground and device chassis. This ground reference always exists with devices dependent on a mains power supply and can exist by chance with battery operated devices.

The present invention advantageously allows measuring, control, and indication arrangements to be connected to the center region of the voltage divider, as provided for in preferred embodiments. The resistors of the voltage divider thus act at the same time as series resistors for reducing the voltage to be measured to a value which can be coped with easily. Equally, an energy selection arrangement can be connected to the center region of the voltage divider. This energy selection arrangement comprises a measuring circuit which switches off the high-voltage generator when a preset voltage value is reached or switches it back to reduced power. Compliance with the specified shock energies depends on the energy selection arrangement operating with precision.

In order to avoid having to design the transformer for the high voltage, the branch circuits of the rectifier are made in the form of a voltage multiplier in accordance with preferred embodiments of the invention. This has the further advantage that, with suitable dimensioning and arrangement of the diodes and capacitors of the voltage multiplier which are connected in a conventional manner, the high voltage generator supplies a voltage which increases as the voltage at the capacitor increases. The result of this is that the efficiency of the high-voltage generator is considerably increased compared with those embodiments which supply a constant voltage and in which when the capacitor is discharged a large proportion of the power is lost in a series resistor or internal resistor of the high-voltage generator. This increase in efficiency of the high-voltage generator is especially important for portable devices because these are supplied from a battery contained in the device, and for reasons of weight and space the capacity of this battery cannot be very large. It is therefore particularly important to make sparing use of the energy stored in the battery.

In the case of the defibrillators described here, it is useful if in addition an electrocardioscope is fitted whose measuring terminals are connected to the electrodes of the defibrillator. The connection can be opened through one set of contacts on a change-over switch in order to protect the amplifier of the electrocardioscope from the destructive effects of the high voltage of the shock. By connecting the measuring terminals of the electrocardioscope to the electrodes of the defibrillator it is unnecessary to use additional electrodes when tracing an electrocardiogram. The arrangement according to the present invention with the potentials of the two capacitor terminals being located roughly symmetrically to chassis now makes it possible, as provided for in a preferred embodiment, to use a switching relay, and in particular a vacuum switching relay, with only two switchover contacts, the common terminal of each switchover contact being connected to the electrodes and the two contacts, which can be selectively connected to the common terminal, being connected to the shunt capacitor or to the measuring terminal of the electrocardioscope. Thus, in contrast to the arrangement described at the outset, it is possible to effect two-terminal switchover both of the electrocardioscope and of the shunt capacitor by means of only two switchover contacts in contrast to the four switchover contacts which were previously necessary. It is thus also possible to use commercial vacuum switching relays which operate rapidly and reliably and which feature the required high-voltage strength while occupying little space.

Figure 2:
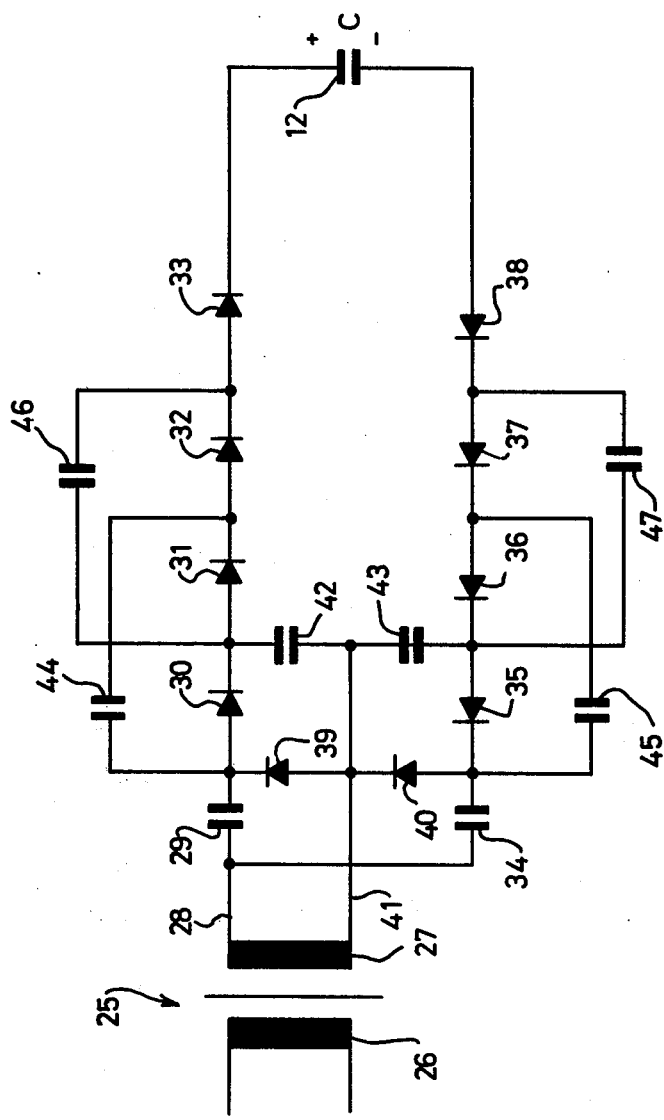
Figure 3:
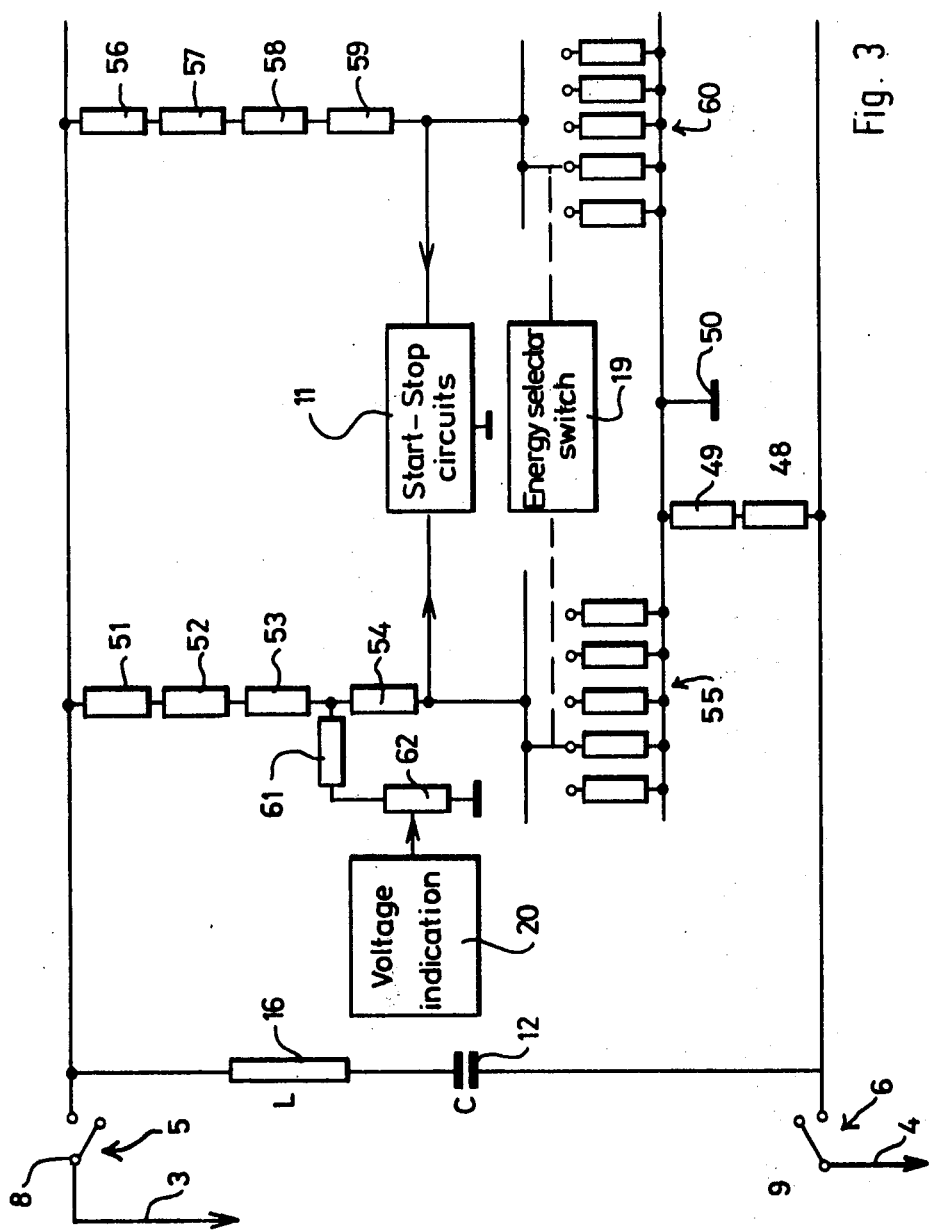

Further details and embodiments of the present invention will become apparent from the following description of a practical example shown in simplified and schematic form in the drawing. In the drawing:

FIG. 1 a block circuit diagram of a defibrillator with cardioscope,

FIG. 2 the circuit of the secondary side of the high-voltage generator including shunt capacitor, and FIG. 3 a basic circuit diagram of the energy selection, charge limiting, and voltage indication circuits.

The device comprises two electrodes 1 and 2 for attaching to the patient, each electrode having a handle and an electrode plate 1' and 2' respectively which are connected through cables 3 and 4 to a switchover contact 5 and 6 respectively on a shock relay 7 which is designed in the form of a two-pole vacuum switching relay. The cables 3 and 4 are each taken to a common pole 8 and 9 of the sets of switchover contacts 5 and 6 respectively.

A charging relay 10 is connected to a switch 1'' provided in the handle of the charging electrode 1 and this relay controls, through a start-stop circuit 11, the charging of a shunt capacitor or defibrillation capacitor 12. To accomplish this, the charging relay 10 switches on, through the start-stop circuit 11, a high-voltage generator 13 which is supplied from a battery 14. The charging relay 10 also switches off an internal discharging device 15 which is connected to the two terminals of the shunt capacitor 12. An inductance 16 is provided in series to the shunt capacitor 12 for the purpose of pulse shaping in order to give the discharge current curve a physiologically optimum form. Two independent voltage measuring devices 17 and 18 are connected to the shunt capacitor 12. Connected to the two voltage measuring devices 17 and 18 is a multiple selector switch 19 which switches off, through the start-stop circuit 11, the high-voltage generator 13 When a preset voltage value is reached corresponding to a specific quantity of energy contained in the shunt capacitor 12. Also connected to the voltage measuring device 18 is an indicator 20 which may be in the form of a series of light-emitting diodes or similar.

Fitted in the handle of the shock electrode 2 is a pressure switch 2'' which is connected to a change-over switch 21 which can be switched over into the "synchronize" position and into the "direct" position. In the latter position, it is connected to an interlock circuit 22 through which the shock relay 7 can be driven. In the other position, the change-over switch 21 establishes a connection to a synchronization circuit 23 to which a synchronizing signal is supplied from the cardioscope through a conductor 24; dependent on this synchronizing signal, the synchronizing circuit 23 controls the shock relay 7 through the interlock circuit 22.

The two normally closed contacts of the sets of switchover contacts 5 and 6 are connected to the cardioscope, whereas the two normally open contacts of the sets of switchover contacts 5 and 6 are each connected to one of the two terminals of the shunt capacitor 12. Thus in the off-position of the shock relay 7 the two electrode plates 1'' and 2'' are connected to the cardioscope, and in the on-position of the shock relay 7 they are connected with the shunt capacitor 12. In the latter case, the cardioscope is switched off at both terminals whereas when the shock relay 7 is in the non-activated state the shunt capacitor 12 is switched off at both terminals.

Referring to FIG. 2, apart from the oscillatory or chopper circuit on the primary side that is not shown in the drawing, the high-voltage generator 13 comprises a transformer 25 whose primary winding 26 is connected to the aforesaid oscillatory or chopper circuit on the primary side. In the secondary winding 27 of the transformer 25, the primary voltage of approximately 9.5 $V_{eff}$ is increased on the secondary side to approximately 630 $V_{eff}$. Both terminals of the shunt capacitor 12 are connected to one end 28 of the secondary winding 27 through a series of diodes and one capacitor in each case, a capacitor 29 and series circuited diodes 30, 31, 32 and 33 leading to the plus terminal of the shunt capacitor 12, and in each case the cathode of the one diode is connected to the anode of the next diode and the cathode of diode 33 is connected to the plus terminal of the shunt capacitor. In addition, another capacitor 34 is connected on one side to the end 28 of the secondary winding 27 and on the other side it is connected to the minus terminal of the shunt capacitor 12 through the series circuit of diodes 35 to 38, the anode terminal of diode 38 being connected to the shunt capacitor 12 and furthermore diodes 35 to 38 are connected from anode to cathode in series. At the junction between capacitor 29 and diode 30, a diode 39 is connected with its cathode and on the other side it is connected to the other end 41 of the secondary winding 27. With this end 41, the cathode of another diode 40 is connected whose anode is connected to the junction between the capacitor 34 and the diode 35. Furthermore, a capacitor 42 is connected between the end 41 and the junction between the diodes 30 and 31, and a capacitor 43 is connected between the end 41 and the junction of diodes 35 and 36. Finally, a capacitor 41 is also placed in parallel to the series circuited diodes 30 and 31 and a capacitor 45 is placed in parallel to the series circuited diodes 35 and 36. A capacitor 46 is placed in parallel to the series circuited diodes 31 and 32 and a capacitor 47 is placed in parallel to the series circuited diodes 36 and 37. The circuit shown in FIG. 2 thus represents a voltage multiplier circuit comprising two rectifier branches and generating a variable output voltage the magnitude of which depends on the charging voltage at the shunt capacitor 12. The effect of this is that the shunt capacitor 12 is charged in the same manner as from a constant current source without it being necessary for a resistor or other energy-consuming element be connected in the feed line to the shunt capacitor 12, which would adversely affect the efficiency of the arrangement.

The circuit with two voltage multiplier rectifier branch circuits also allows the measurement and control arrangement to be formed as shown in FIG. 3. One terminal of the shunt capacitor 12 is connected to a reference point or the device chassis 50 through the series circuiting of two resistors 48 and 49 which are part of voltage dividers. Furthermore, there is a connection between the other terminal of the shunt capacitor 12 and the device chassis 50 through a chain of resistors comprising four series circuited resistors 51 to 54 and a resistor which may be included in the circuit from a goup of resistors 55 which are connected jointly with one terminal to the device chassis 50 and from which any one can be selected to be connected to the resistor 54 by means of the multiple selector switch 19. In parallel to the resistors 51 and 54 and the group of resistors 55 there is an identical series of resistors 56 to 59 and a group of resistors 60 which are constructed and arranged symmetrically to the first-mentioned resistors and the first-mentioned group of resistors. The inputs of the start-stop circuit 11 are connected to the junction between the resistor 54 and the group of resistors 55 and to the junction between the resistor 59 and the group of resistors 60. The indicator 20 is connected to the junction between the resistors 53 and 54 through a series resistor 61 and a potentiometer 62. The input of the indicator 20 is connected to the wiper of the potentiometer 62 of which one end is connected to the series resistor 61 and the other end with the device chassis 50.

The multiple selector switch 19 selects symmetrically in each of the two branches one resistor from the group of resistors 55 and from the group of resistors 60 and this results, in accordance with the exemplary embodiment, in the shunt capacitor being charged to an energy content of 50, 100, 200, 300 or 400 joule. Switch-off of the high-voltage generator 13 and thus the termination of the charging process depends on a preset voltage at the capacitor, this voltage being supplied to the start-stop circuit 11 reduced proportionately by the voltage divider. This circuit includes one voltage discriminator in each case which responds to a fixed preset voltage. This fixed preset voltage, however, corresponds to various voltages at the shunt capacitor 20 depending on the position of the multiple selector switch 19, and is selected such that the shunt capacitor 12 always has the desired energy content.

As a result of the described arrangement, the two terminals of the capacitor each have about the same potential difference to the device chassis, and thus the insulation problem is considerably reduced. Owing to the high-impedance "binding" of the high-voltage section through the voltage dividers (48 to 60) a high leakage current safety is obtained because even in the most unfavourable case the leakage currents are so small that they can be completely ignored from a physiological aspect. For example, the values of the resistors 48, 49 and 51 to 54 and 56 to 59 are in each case 10 Mohm. A further advantage is that in this manner the potential of the transformer secondary winding 27 is approximately zero with respect to device chassis, and thus the transformer need be insulated as far as the voltage strength is concerned only against the voltage produced by the secondary winding but not with respect to the high voltage at the capacitor owing to the combination of the above-mentioned voltage divider with the design of the rectifier with branches which are at least approximately electrically symmetrical. Furthermore, this advantageously results in the insulation resistance between this winding and the device chassis causing no unsymmetrical shifting of the potentials at the two terminals of the shunt capacitor relative to the device chassis.

Various modifications can be made without departing from the invention.

Although my invention has been illustrated and described with reference to the preferred embodiments thereof, I wish to have it understood that it is in no way limited to the details of such embodiments, but is capable of numerous modifications within the scope of the appended claims.

Having thus fully disclosed my invention, what I claim is:

1. A voltage generator for charging a shunt capacitor having a pair of terminals connected to the electrodes of electroshock apparatus such as a ventricular and auricular defibrillator comprising, a transformer having a primary winding connected to a source of current and a secondary winding, a rectifier comprises a pair of similar branch circuits connected between the opposed terminals of said shunt capacitor and to the secondary winding of said transformer and a high impedance voltage divider interposed in parallel between said shunt capacitor and said rectifier, the center of said voltage divider being connected to ground, whereby the potential on each terminal of said shunt capacitor relative to ground is substantially equal.

2. The voltage generator according to claim 1 wherein said voltage divider comprises voltage means connected to each of said rectifier branch circuits and ground, voltage measuring means connected to one of said rectifier branch circuits and ground, and voltage indicating means connected to said measuring means and said ground.

3. The voltage generator according to claim 1 wherein said voltage divider includes means for selectively adjusting the voltage output thereof.

4. The voltage generator according to claim 1 in which each of said rectifier branch circuits are similar to each other and comprise voltage multipliers.

5. Medical appliance comprising a defibrillator having a pair of electrodes, and an electrocardioscope having a pair of terminals, switch means comprising a relay having a two pairs of fixed terminals and a pair of movable contacts connected respectively to one of said electrodes, one of said pairs of fixed terminals being connected respectively to the terminals of said electrocardioscope and the other of said pair of fixed terminals being connected respectively to the terminals of a shunt capacitor having a voltage generator according to claim 1.

* * * * *